United States Patent [19]
Chow

[11] Patent Number: 5,048,321
[45] Date of Patent: Sep. 17, 1991

[54] METHOD OF DISCRIMINATING BREATH CONTAMINANTS AND APPARATUS THEREFOR

[75] Inventor: G. Daniel Chow, Richmond, Calif.
[73] Assignee: Intoximeters, Inc., St. Louis, Mo.
[21] Appl. No.: 522,313
[22] Filed: May 11, 1990
[51] Int. Cl.$^5$ ............................................. G01N 19/02
[52] U.S. Cl. ..................................... 73/23.3; 73/23.2; 73/23.23; 422/84
[58] Field of Search .................. 73/23.3, 23.2; 422/84

[56] References Cited

U.S. PATENT DOCUMENTS

| | | | |
|---|---|---|---|
| 4,090,078 | 5/1978 | Heim | 73/23.3 |
| 4,487,055 | 12/1984 | Wolf | 73/23.3 |
| 4,770,026 | 8/1988 | Wolf | 73/23.3 |
| 4,809,810 | 3/1989 | Elfman et al. | 422/84 |

OTHER PUBLICATIONS

"Intoxicometer 3000–Supervisor Manual", Copyright 1980, Caldetect, Inc., pp. 18–21.

Primary Examiner—Robert Raevis
Assistant Examiner—W. Francos
Attorney, Agent, or Firm—Polster, Polster and Lucchesi

[57] ABSTRACT

A method of discriminating alcohols different from ethanol in breath samples includes sampling voltages from a fuel cell at a rapid rate to establish a curve rising, upon introduction of a sample containing a known amount of ethanol without interferants, from an initial base line to a peak; determining a peak voltage; establishing an end point; determining the area under the curve from the introduction of the sample to the end point, and determing at least two other areas under the curve between the peak and the end point, a peak area, between the peak and a point on the curve relatively near the peak, and a trail area, between the end point and a point nearer the end point than the peak area; introducing to the fuel cell a breath sample that may contain an interferant in the form of an alcohol different from ethanol, and determining the peak voltage, end point, total area, peak area and trail area using the same criteria as were used in determining those pieces of information in connection with the sample containing only ethanol, and comparing the pieces of information electronically.

7 Claims, 2 Drawing Sheets

METHOD OF DISCRIMINATING BREATH CONTAMINANTS AND APPARATUS THEREFOR

BACKGROUND OF THE INVENTION

One of the weaknesses of conventional breath alcohol testing equipment is its inability to discriminate volatile constituents of the breath different from ethanol which produce an output from an infra-red cell. Various methods and apparatus have been proposed to discriminate these contaminants, and some of them are quite effective in detecting such things as toluene, but none has been effective in detecting alcohols closely related to ethanol, such as methanol, propanol and isopropanol. The burden of proof in cases involving driving while intoxicated, when the evidence is the result of a breath test, has become heavy in many jurisdictions, and it is important to be able to convince a court that the result was not anomalous by virtue of the presence of methanol, for example.

In the method of the present invention, amounts of methanol constituting as little a five percent of the total alcohol content of breath samples can be detected.

One of the objects of this invention is to provide a method of discriminating contaminants in the nature of alcohols different from but closely related to ethanol in a breath alcohol testing device.

Another object is to provide apparatus for accomplishing the method.

Other objects will become apparent to those skilled in the art in the light of the following description and accompanying drawing.

SUMMARY OF THE INVENTION

In accordance with this invention, generally stated, a method of discriminating contaminants in the course of breath alcohol testing includes providing a fuel cell and an infra-red cell and means for supplying a breath sample to both, producing and measuring an output from the infra-red cell to establish an apparent breath alcohol measure; defining a curve of the voltage output of the fuel cell against time, determining the height and position of the peak voltage of the fuel cell output, establishing a cut-off or end point, which can be, for example, a predetermined fraction of the voltage difference between an initial base line voltage and the peak voltage, measuring a first selected area under the curve from the peak to a point that can be determined as a function of the time from peak to end point, measuring a second area under the curve from a second point, closer to the end point than the first selected area, which can be determined as a function of the time from peak to the end point, determining the total area under the curve from the initiation of the test to the end point, and comparing electronically the position of the peak, the total area, the first area and the second area with those elements of a curve produced by a known standard sample containing only ethanol in a concentration of a magnitude with that indicated by the output of the infra-red cell. If these measurements are inconsistent with one another, it indicates that a contaminant (interferant) is present. The nature of the fuel cell is that it is not sensitive to non-alcohol interferants, but in the method of this invention, is sensitive to alcohol interferants different from ethanol, while the nature of the IR system is that it responds to interferants both in the form of alcohols different from ethanol, and also non-alcohol interferants. Accordingly, if the fuel cell curve profile and its included area imply a certain ethanol value, and the IR output value exeeds that value, the interferant is considered to be non-alcohol. In the method of this invention, the nature of the alcohol interferant is also revealed, particularly if the interferant is one of the alcohols most likely to be observed in human breath. Thus, for example, if the second area under the curve generated by the fuel cell is higher than the standard, the first area being substantially the same as the standard, methanol is the contaminant. If the second area is the same but the first area different, the contaminant is isopropanol.

Preferably, the apparatus includes a conventional infra-red cell and, a fuel cell circuit basically similar to the one described in U.S. Pat. No. 4,770,026, with a rapid voltage drop-off, falling to a substantially steady state within a time on the order of two minutes or less. As explained in U.S. Pat. No. 4,770,026, the basic function of a fuel cell in a breath alcohol testing device of the type sold commercially, as for example the device sole by Intoximeters Inc., 1901 Locust Street, St. Louis, MO under the trademark ALCO-SENSOR, is to oxidize alcohol in a breath sample passed over it, the resulting voltage due to the flow of electrons obtained from that oxidation being measured across a resistor. The voltage generated is a function of breath alcohol content. In the method of that patent, rather than measuring simply the peak voltage, the entire area under the curve is integrated, either directly or by interpolation, but the result is still a function of the amount of oxidizable substance in the breath. Normally this is ethanol, but the method of this invention provides means for discriminating even between methanol and ethanol.

The conventional infra-red system consists of an elongated tube divided into two long chambers by a longitudinally extending partition. One of the chambers receives a breath sample; the other provides a reference standard. Infra-red energy is generated at one end of the tube by a nichrome helix heated, in response to electric current, to around 800° C. The source energy is modulated at two different rates with respect to the two different chambers by a slotted chopped wheel, so that a single detector with demodulation can differentiate between the energy transmitted through the two chambers. A description of the conventional IR device and method is given in a booklet entitled "Intoximeter 3000 Supervisor Manual", published in 1980, and republished since. Each compound in the breath absorbs infra-red energy in a combination of absorption bands at frequencies unique to the compound. The positions of the absorption bands do not change, but the amount of energy absorbed at a given absorption band varies in direct relation to the number of molecules within a fixed path, e.g. the concentration of alcohol in the breath sample chamber. By using a narrow band pass interference filter to isolate an absorption band that is a strong absorption band for alcohol and using as a reference the contents of the reference standard chamber, which contains no alcohol, the amount of energy attenuated will be proportional to the number of alcohol molecules in the sample cell. As is explained above, the IR system may also respond to interfering substances, but without discriminating between or among them. The fuel cell system can, and in the present method, does discriminate, thus providing a check against the result of the IR measure.

As has been indicated, preferably the method of this invention is applied to apparatus that includes both a conventional infra-red cell and a fuel cell circuit. However, the method of this invention applied to the fuel cell alone gives significant information. Means are provided by which readings of the output voltage from the fuel cell are taken rapidly, in the preferred embodiment described, on the order of twenty five hundred times per second, clearly to define a curve of voltage versus time, and to establish accurately the time to peak, the amplitude of the peak, and the points at which the first and second areas begin and end. The particular circuit of the preferred embodiment includes some refinements that are not essential to the claimed invention, but represent the best mode known to applicant.

DESCRIPTION OF PREFERRED EMBODIMENT

Figure 4:
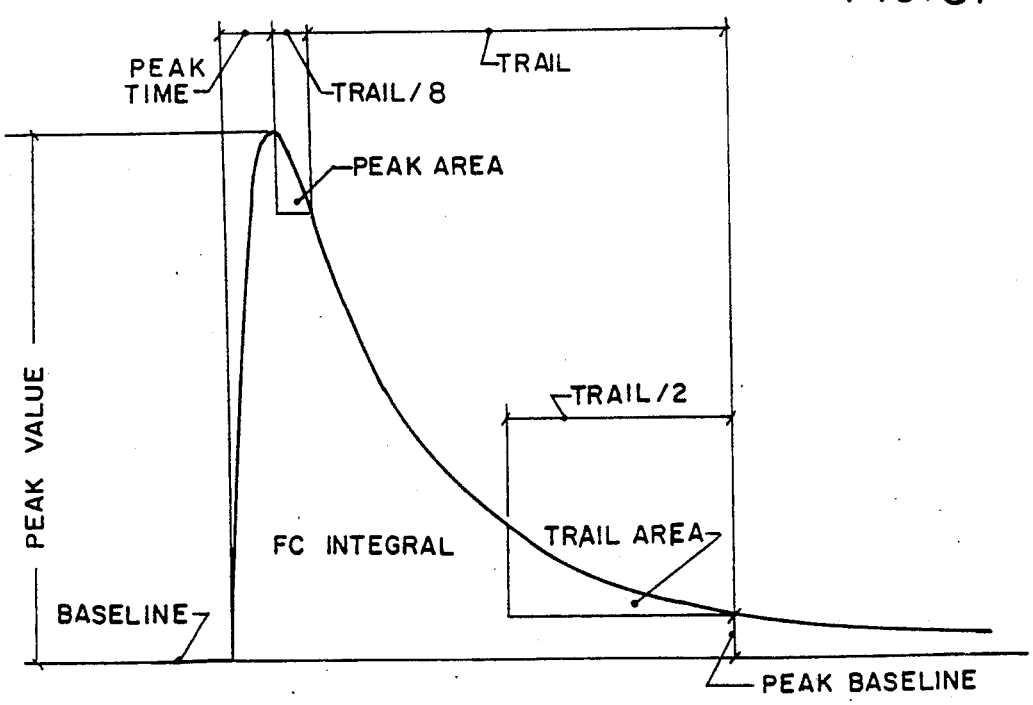
FIG. 4 is a curve representing the output from a suitable fuel cell exposed to a standard sample containing 0.10 percent ethanol, in which criteria used in the method of this invention are illustrated.

Referring now to FIG. 4, the figure shows a plot of data representing the voltage output of a fuel cell of the type described in U.S. Pat. No. 4,770,026, with a resistance across the terminals of the fuel cell high enough to permit the voltage from the fuel cell to be measured accurately, but low enough to fall to a substantially steady minimum voltage in a relatively short time, for example, a voltage drop-off to steady state within two minutes or less, following the introduction of a sample containing 0.10 gram percent ethanol. The measurement of voltage (A/D count) is made frequently, for example twenty five hundred (2,500) times a second. An initial base line voltage is established and measured before a sample is introduced to the fuel cell. Ideally, the initial base line voltage is zero, but, depending upon the characteristics of the instrument, it may be considered desireable to introduce a small positive voltage initially, in this instance, 0.03 volts. After the sample is introduced, in this particular apparatus, the peak voltage of 1.00 volts is reached after 2.0 seconds. Both the peak voltage and the time from the beginning of the rise in voltage to the peak are stored. In this illustrative example, an end point is established after the determination of the peak voltage, when the voltage reaches one tenth (10 percent) of the voltage representing the difference between the initial baseline voltage and the peak voltage (base-to-peak voltage rise), which, in this case, is after an elapsed time of 16 seconds after the peak voltage is reached, and this information is also stored. The voltage at this point (0.97v) establishes a second baseline, sometimes called the trail baseline, because the portion of the curve following the peak is sometimes referred to as the trail.

Three areas under the curve are determined. The total area from the start of the rise of voltage upon the introduction of the sample to the cut-off or end point; a peak area, between the peak of the curve and a peak area base line determined by a point, which, in this illustrative embodiment, is determined as the voltage at a time that is one eighth of the time elapsing between the peak and the end point (here 2 seconds); and a trail area above the end point base line between the end point and a point on the curve, which, in this embodiment is determined as the voltage at a time that is one half of the time elapsing between the peak of the curve and the end point (8 seconds). These pieces of information are also stored.

With these pieces of information, alcohol contaminants that have heretofore been extremely difficult to discriminate consistently, can readily be detected.

Figure 2:
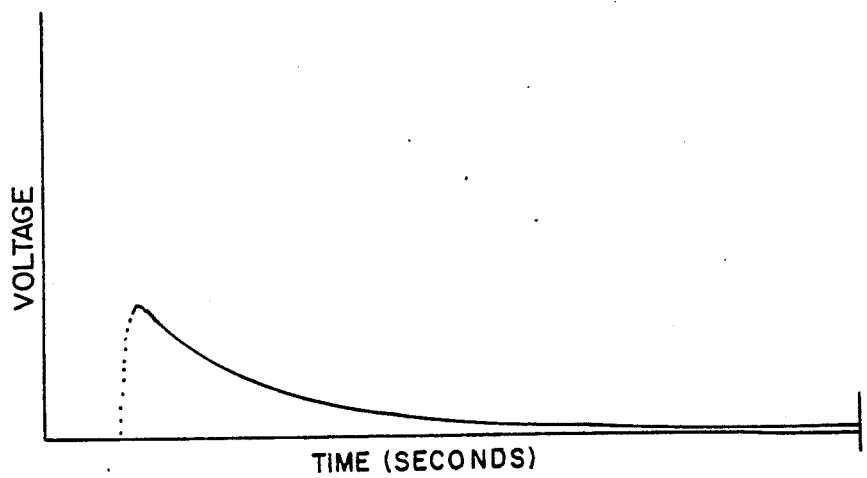
FIG. 2 is a curve representing the output from a fuel cell exposed to 0.10 percent isopropanol in an inert gas carrier.

Referring now to FIG. 2, which shows a plot of voltage output from a fuel cell into which 0.1 percent isopropanol has been introduced, it can be seen that the slope of the curve following the peak is different from the slope of the curve of FIG. 4, hence the peak area as determined in the same way as the peak area of FIG. 4 will be different from the peak area under the curve shown in FIG. 4, although the tail area is much the same as that of the curve shown in FIG. 4.

Figure 3:
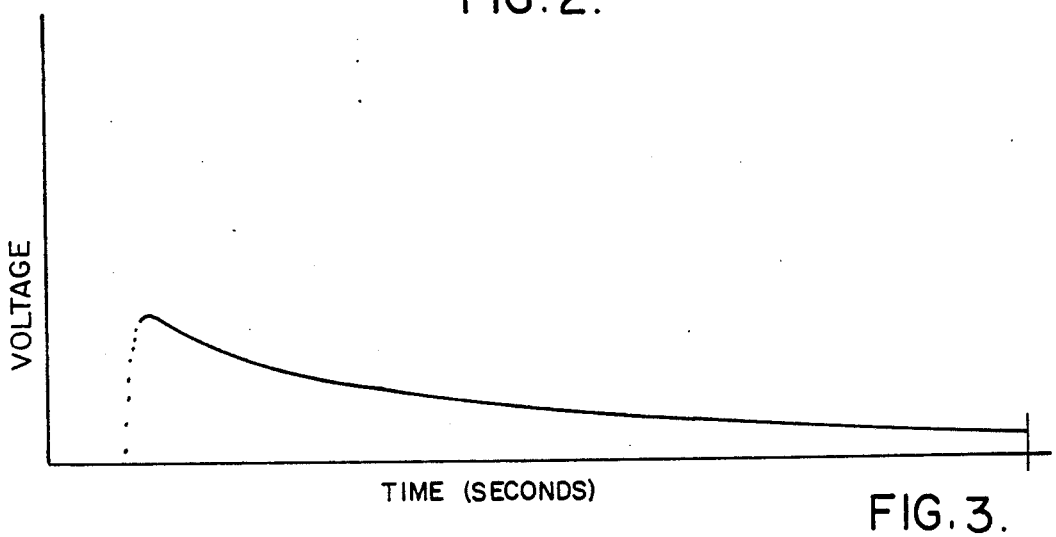
FIG. 3 is a curve representing the output from the same fuel cell exposed to a sample containing 0.10 percent methanol.

Referring to FIG. 3, which shows a plot of voltage output from a fuel cell into which 0.1 percent methanol has been introduced, it can be seen that, although the peak area is similar to that obtained in FIG. 3, the tail area is substantially greater.

A sample containing both methanol or isopropanol and ethanol will share characteristics of both curves, but the anomolies resulting from the presence of the interferant will be readily detected.

Figures 1, 1A:
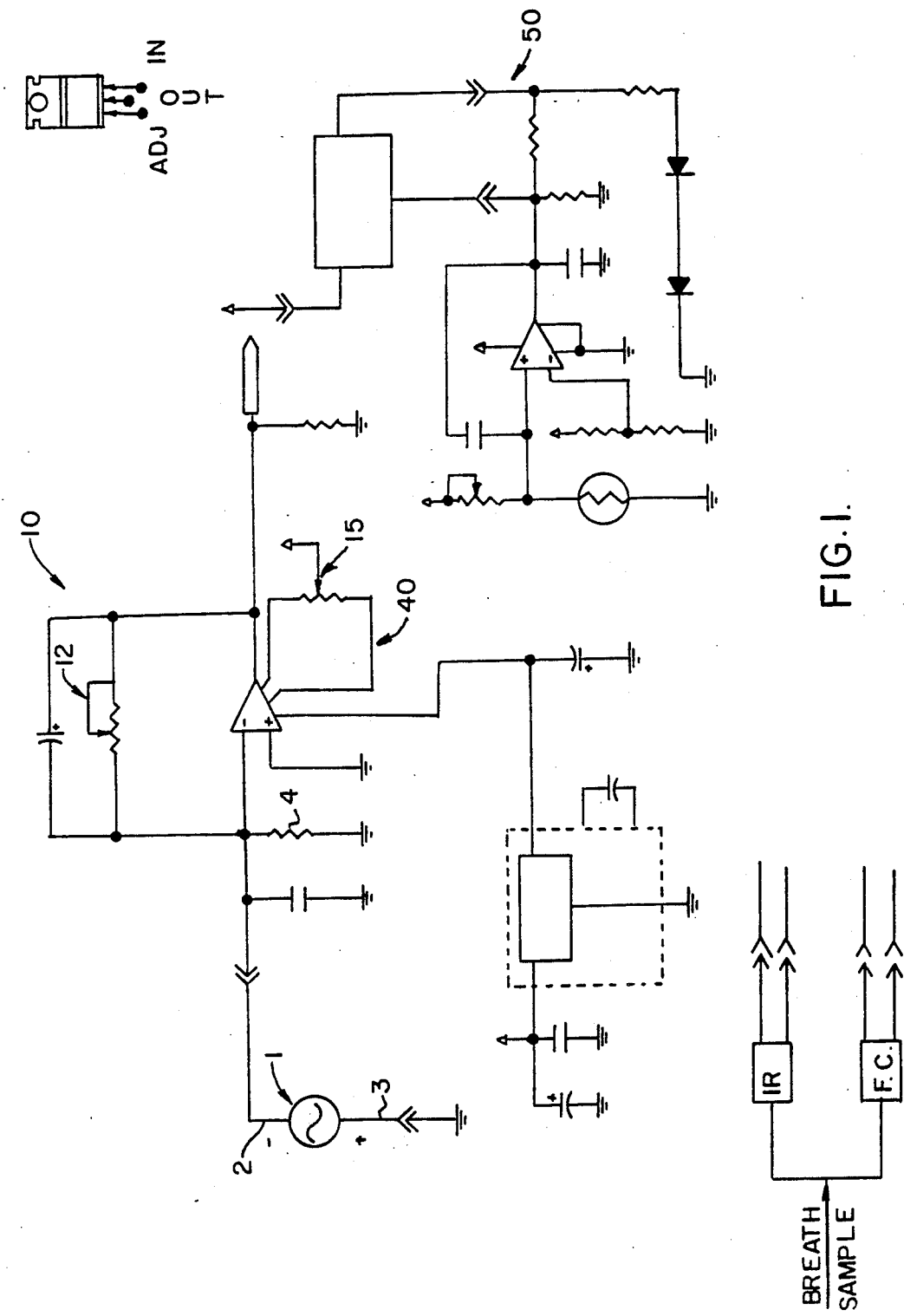
FIG. 1 is a circuit diagram, showing one embodiment of circuit suitable for carrying out the method of the invention.
FIG. 1A is a diagram showing analysis of breath sample by both an infrared and fuel cell system.

The apparatus by which these various criteria are established is illustrated diagrammatically in FIG. 1. It is basically the circuit shown in Wolfe U.S. Pat. No. 4,770,026, with the addition of a negative feed back loop 10 with a variable resistor 12 so that the gain on the fuel cell signal can be varied. Another variable resistor 15 in an offset circuit 40 is provided to permit adjusting the offset from the peak voltage as has been described. Thus, the circuit consists essentially of a fuel cell 1, with terminals 2 and 3 across which a resistor 4 is connected, as is the resistor 4 of the Wolfe patent circuit. In the present circuit, the resistance 4 is a 1.2 ohm resistor, which provides an even more rapid clean up time than the Wolfe circuit described. In this embodiment, a five volt regulator is connected to the operational amplifier 10, as is the off set circuit 40. A temperature control circuit 50 is also illustrated, to maintain a constant temperature of the fuel cell housing, but it forms no part of this invention.

An infra-red system is not illustrated, because such systems are conventional, and their use is well understood. The function of an IR system used with the fuel cell system of this invention, is to facilitate standardization of the fuel cell, to determine the magnitude of alcohol content of a breath sample and to combine the ability to discriminate interferants of both alcohol and non-alcohol types in one instrument.

Numerous variations in the apparatus and method of this invention, within the scope of the appended claims will occur to those skilled in the art in the light of the foregoing disclosure. Merely by way of example, although the method described of determining the peak and trail areas, and the end point is the preferred method, and has advantages that have led to its adoption, the end point can be determined as a function of time rather than as a function of the change of voltage from the differential voltage, when the characteristics of the instrument have been determined. Similarly, the peak and trail areas can be determined by setting points on the curve as a function of change in voltage, and measuring time to those points as well as subtended area as criteria of differences from the standard ethanol curve. It is important to sample at a rapid rate to establish accurately the profile of the curve. The A/D count can be slower than 2500 per second; the method can be carried out at a hundred counts per second, for example, but the accuracy of the method is enhanced by more rapid sampling. These are merely illustrative.

Having thus described the invention, what is claimed and desired to be secured by Letters Patent is:

1. A method of discriminating alcohols different from ethanol in breath samples comprising sampling voltages from a fuel cell at a rapid rate to establish a curve rising, upon introduction of standard samples containing a known amount of ethanol without interferants, from an initial base line to a peak; establishing an end point; determining the area under the curve from the introduction of the sample to said end point, and establishing at least two other areas under the curve between the peak and the end point, a peak area, between the peak and a point on the curve relatively near the peak, and a trail area, between the end point and a point nearer the end point than the peak area; introducing a sample containing interferants in the form of alcohols different from ethanol and detecting said interferants by establishing differences between the values calculated based on total areas and the peak and trail areas of curves generated in response to said sample containing said interferants and those of said standard sample containing ethanol alone.

2. The method of claim 1 wherein the end point is determined as a function of the voltage rise from the time of introduction of the sample, and the peak and trail area points are determined as functions of the time elapsing between the peak and the end point.

3. The method of claim 1 wherein said rate of sampling is on the order of twenty-five hundred times a second.

4. A method of discriminating breath contaminant in a breath alcohol detecting and measuring device comprising providing a fuel cell and an infra-red cell and means for supplying a breath sample to both, producing and measuring an output from said infra-red cell to establish an apparent breath alcohol measure; defining a curve of the voltage output of said fuel cell against time, determining the height and position of the peak voltage of said fuel cell output, establishing an end point, measuring a first selected area under said curve from said peak to a first point that is a function of time or voltage following the peak, measuring a second area under said curve from a second point that is a function of time or voltage following the peak, determining the total area under said curve to said end point, and comparing electronically the position of said peak, the total area, the said first area and the said second area with those elements of a curve produced by a known standard sample containing only ethanol in a concentration of a magnitude with that indicated by the output of said infra-red cell.

5. The method of claim 4 wherein the end point is determined as a function of the voltage rise from the time of introduction of the sample, and the peak and trail area points are determined as functions of the time elapsing between the peak and the end point.

6. The method of claim 4 wherein said rate of sampling of the fuel cell is on the order of twenty-five hundred times a second.

7. The method of claim 5 wherein said rate of sampling is on the order of twenty-five hundred times a second.

* * * * *